United States Patent
Bibette et al.

(10) Patent No.: US 6,627,603 B1
(45) Date of Patent: Sep. 30, 2003

(54) METHOD FOR RELEASING AN ACTIVE PRINCIPLE CONTAINED A MULTIPLE EMULSION

(75) Inventors: Jérôme Bibette, Bordeaux (FR); Marie-Françoise Ficheux, Gradignan (FR); Fernando Leal Calderon, La Brede (FR); Lida Bonnakdar, Talence (FR)

(73) Assignee: Centre National de la Recherche Scientifiquue (C.N.R.S.), Paris (FR)

( * ) Notice: Subject to any disclaimer, the term of this patent is extended or adjusted under 35 U.S.C. 154(b) by 0 days.

(21) Appl. No.: 09/284,062

(22) PCT Filed: Aug. 5, 1998

(86) PCT No.: PCT/FR98/01748

§ 371 (c)(1),
(2), (4) Date: Aug. 10, 1999

(87) PCT Pub. No.: WO99/07463

PCT Pub. Date: Feb. 18, 1999

(30) Foreign Application Priority Data

Aug. 7, 1997 (FR) ............................................ 97 10154

(51) Int. Cl.⁷ .......................... A61K 38/28; A61K 9/00; A61K 38/43; A61K 47/00
(52) U.S. Cl. .......................... 514/3; 424/94.1; 424/400; 424/401; 514/769; 514/772; 514/784; 514/785; 514/873; 514/885; 514/904; 514/913; 514/937; 514/938; 514/941; 514/942; 514/943; 514/969; 514/974; 514/975
(58) Field of Search ................................ 514/772, 873, 514/904, 937, 938, 942, 943, 969, 975, 3, 769, 784, 785, 885, 913, 941, 974; 424/400, 401, 94.1

(56) References Cited

U.S. PATENT DOCUMENTS 5,444,041 A * 8/1995 Owen et al. .................... 514/2
5,688,761 A * 11/1997 Owen et al. .................... 514/2

FOREIGN PATENT DOCUMENTS

DE 195 09 301 9/1996
EP 0 717 978 6/1996

OTHER PUBLICATIONS

Omotosho et al., J. Microencapsulation (1989), vol. 6, No. 2, pp. 183–192.*

* cited by examiner

Primary Examiner—Jose' G. Dees
Assistant Examiner—Frank Choi
(74) Attorney, Agent, or Firm—Young & Thompson

(57) ABSTRACT

A method for the controlled release of an active principle contained in a multiple water-in-oil-in-water emulsion characterized in that the multiple emulsion comprises an invert emulsion Ei with an aqueous phase A1 containing at least a hydrophilic active principle. The emulsion Ei is dispersed in the form of direct emulsion droplets Ed, in a continuous aqueous phase A2, with the two emulsions Ed and Ei stabilized by at least a surfactant, present in their respective continuous phases. The multiple emulsion is brought in the presence of an effective amount of an agent for transforming it into a direct emulsion and induce the release of the active principle, contained in the aqueous phase A1 of emulsion Ei, in the aqueous phase A2.

9 Claims, 2 Drawing Sheets

METHOD FOR RELEASING AN ACTIVE PRINCIPLE CONTAINED A MULTIPLE EMULSION

This application is a 371 of PCT/FR98/01748, filed Aug. 5, 1998.

BACKGROUND OF THE INVENTION

The subject-matter of the present invention is a process for releasing an active principle present in a multiple emulsion.

By definition, an emulsion consists of a dispersion of two mutually immiscible phases, such as generally a mixture of an aqueous phase and an oily phase. An emulsion is known as a direct emulsion when it comprises oil droplets dispersed in an aqueous phase, and as an inverse emulsion when it comprises water droplets dispersed in an oily phase.

Emulsions are conventionally obtained by shearing one of the phases within the other phase in the presence of at least one surfactant of the type: surface-active agents, polymers, and the like.

These surfactants are in fact chosen according to the nature of the emulsion envisaged. In the case of a direct emulsion, surfactants possessing a hydrophilic/lipophilic balance (HLB) of greater than 14 are favoured. On the other hand, surfactants with an HLB of less than 7 are preferably employed in inverse emulsions.

The term "HLB" (Hydrophilic Lipophilic Balance) denotes the ratio of the hydrophilicity of the polar groups of the surface-active molecules to the hydrophobicity of the lipophilic part of these same molecules; this is a term commonly used in the field of surfactants (see the treatise, "Techniques de l'Ingénieur" ["Techniques of the Engineer"], chapter A7610: "Les agents de surface" ["Surfactants"].

The emulsions incorporating these surfactants remain metastable for a sufficiently long period of time to allow them to be economically exploited in numerous fields of application, such as, for example, the cosmetic, coating, food and pharmaceutical industries.

In the specific case of multiple emulsions, at least two emulsions are superimposed. This relates, for example, to a dispersion, in an aqueous phase, of oily globules in which are dispersed tiny water droplets. Each of these two emulsions is, of course, stabilised by virtue of the incorporation, in its continuous phase, of a surfactant as defined above.

The present invention is targeted specifically at taking advantage of this type of water-in-oil-in-water multiple emulsion in order to transport at least one hydrophilic active principle and to allow its release in a controlled way.

Because of its three-phase structure, a water-in-oil-in-water multiple emulsion proves advantageously favourable to the encapsulation, in its internal water droplets, of hydrophilic active principles. The globules of the oily phase, in which globules the said water droplets are emulsified, confer an excellent protective barrier to the said principles with respect to the external environment. The transportation of these active principles via the multiple emulsion can thus be envisaged.

The object of the present invention is specifically to provide a process which makes it possible to control the release of this active principle encapsulated in a multiple emulsion.

Within the meaning of the present invention, "multiple emulsion" is understood to define a water-in-oil-in-water emulsion comprising an inverse emulsion, Ei with an aqueous phase A1, in dispersion in the form of droplets of direct emulsion Ed, in a continuous aqueous phase A2, with the two emulsions Ed and Ei comprising, in their respective continuous phases, at least one surfactant in an amount sufficient to maintain them in stabilized and differentiated forms within the said multiple emulsion. The hydrophilic active principle present in the multiple emulsion under consideration according to the invention is present in the aqueous phase A1.

The step used to release this active principle from the multiple emulsion in fact takes advantage of the coalescence phenomena which can appear within the emulsion.

By definition, a coalescence is a breaking of a thin film established between two adjacent drops. In the case of a multiple emulsion, this type of coalescence can arise at two levels, the first between the internal water droplets present in an oily globule and the second between the interface of an oily globule and some of its internal water droplets.

Surprisingly, it proves to be possible to control these coalescence phenomena, that is to say to oppose them or, in contrast, to induce them, by virtue of the use in the said emulsion of specific concentrations of surfactants.

The studies carried out in the context of the present invention have thus made it possible to demonstrate that the coalescence phenomenon which more particularly determines an instability of the multiple emulsion favourable to the release of the active principle present in the internal water droplets A1 is that which takes place at the interface of an oily globule and of some of its internal water droplets A1. This results in a transfer of the active principle, initially present in these water droplets A1, to the aqueous phase A2. The active principle is then in contact with the external environment, originally comprising the said multiple emulsion, and can therefore exert its activity.

It advantageously proves possible to oppose or, in contrast, to induce the appearance of this coalescence phenomenon by intervening at the level of concentration of surfactant in the continuous aqueous phase A2 of the emulsion Ed. There exists a critical concentration threshold beyond which it is possible to trigger the escape of the contents of the internal water droplets A1 to the external environment.

SUMMARY OF THE INVENTION

Consequently, the present invention provides a process for releasing, in a controlled way, an active principle present in a multiple emulsion of water-in-oil-in-water type, characterized in that the said emulsion comprises an inverse emulsion Ei with an aqueous phase A1 in which is incorporated at least one hydrophilic active principle, the said emulsion Ei being dispersed in the form of droplets of direct emulsion Ed in an aqueous phase A2 with the emulsions Ei and Ed stabilized by at least one surfactant present in their respective continuous phases, and in that the said multiple emulsion is brought into the presence of a sufficient amount of an agent to convert it into a direct emulsion, so as to induce the release of the active principle present in the aqueous phase A1 of the emulsion Ei into the aqueous phase A2.

According to a favoured embodiment of the invention, the surfactant involved in the aqueous phase A2 of the emulsion Ed is present at a concentration below its critical concentration threshold.

Within the meaning of the invention, a critical concentration threshold is understood to define the value of surfactant concentration beyond which destabilization of the multiple emulsion is induced with the effect of releasing the active principle.

If the concentration of hydrophilic surface-active agent present in the aqueous phase A2 is below this concentration threshold, then no coalescence is observed for a period of the order of several months.

Conversely, if the concentration of hydrophilic surface-active agent present in the aqueous phase A2 is greater than or equal to this concentration threshold, then coalescence and therefore release take place over a time scale varying from a few days to a few minutes. The higher this concentration, the shorter the release time.

The release of the active principle will be regarded as complete when virtually all the droplets of the aqueous phase A1 have been released into the external aqueous phase A2. The release of the active principle will therefore be assessed as fast or slow according to the time taken to carry out the release of the droplets.

Advantageously, it thus proves to be possible to control the release of the active principle over a longer or shorter period of time by adjusting the difference in concentration between the critical concentration threshold and the final concentration obtained by addition of surfactant.

In fact, it has been observed that this concentration threshold could be expressed with respect to the critical micelle concentration, CMC, of the surfactant under consideration.

The critical micelle concentration is defined as the concentration beyond which the surface-active molecules combine together to form spherical clusters known as micelles (see, for example, "Galenica 5, agents de surfaces et émulsions" ["Surfactants and emulsions"], vol. 5.1, page 101, editor: Techniques et Documentation [Techniques and Documentation] (Lavoisier)).

However, the value of this concentration threshold, expressed with respect to the CMC, also varies according to the HLB value of the surfactant.

Thus, for a certain range of HLB values, the corresponding surfactants should be present in the aqueous phase A2 at a concentration below their critical micelle concentrations, if it is desired to avoid release of the active principle.

On the other hand, for another range of HLB values, the corresponding surfactants may be present up to a concentration far greater than their CMC, without this release of the active principle being observed.

As a general rule, for surfactants having an HLB of the order of 40, that is to say very hydrophilic, the concentration threshold is between 1 and 20 CMC.

In the case of surfactants having an HLB of between approximately 12 and 20, this concentration threshold is greater than 100 CMC.

Likewise, the diameter of the internal water droplets A1, the diameter of the droplets of emulsion Ed, the chemical nature of the active principle present in the aqueous phase A1 and the amount and type of surface-active agent present in the oily phase of the emulsion Ei affect the value of this critical concentration threshold.

All these parameters are therefore to be taken into consideration in assessing the critical concentration threshold for a specific surfactant present in the continuous aqueous phase A2 of the emulsion Ed.

This critical concentration threshold can be easily assessed, for a surfactant of given HLB, from preliminary tests according to the procedure described in Example 1 below.

This assessment can, for example, be carried out according to the procedure which consists in:

preparing a multiple emulsion which incorporates the active principle in its internal aqueous phase and which comprises a surfactant in the external aqueous phase A2 in an amount sufficient to stabilize the said emulsion, adding, to the aqueous phase A2 of the said emulsion, increasing amounts of the said surfactant, quantitatively determining, on conclusion of each addition of the said surfactant, the concentration of active principle which has or has not been released into the external aqueous phase, and recording the concentration of surfactant beyond which a significant acceleration in the release kinetics is observed.

Generally, the concentration of surfactant is recorded beyond which 90% of the active principle initially present within the internal phase is found in the external aqueous phase in a time period of approximately 10 hours.

As regards the technique of quantitative determination used to estimate the concentration of the released active principle, it varies, of course, as a function of the nature of this active principle. It can be a conductimetric or potentiometric measurement, when the active principle is an ionic species, or alternatively a fluorescence spectroscopy technique, if the active principle is fluorescent.

Of course, a person skilled in the art is in a position to select the appropriate quantitative determination technique.

Advantageously, it therefore proves to be possible to induce the release of the active principle present in the claimed emulsion by bringing the direct emulsion Ed into contact with an agent, such that it causes, because of its presence and optionally its concentration, a transfer of the internal water droplets A1 to the aqueous phase A2, thus converting the multiple emulsion into a simple direct emulsion with release of the active principle into the external environment.

DETAILED DESCRIPTION OF THE INVENTION

Figure 1:
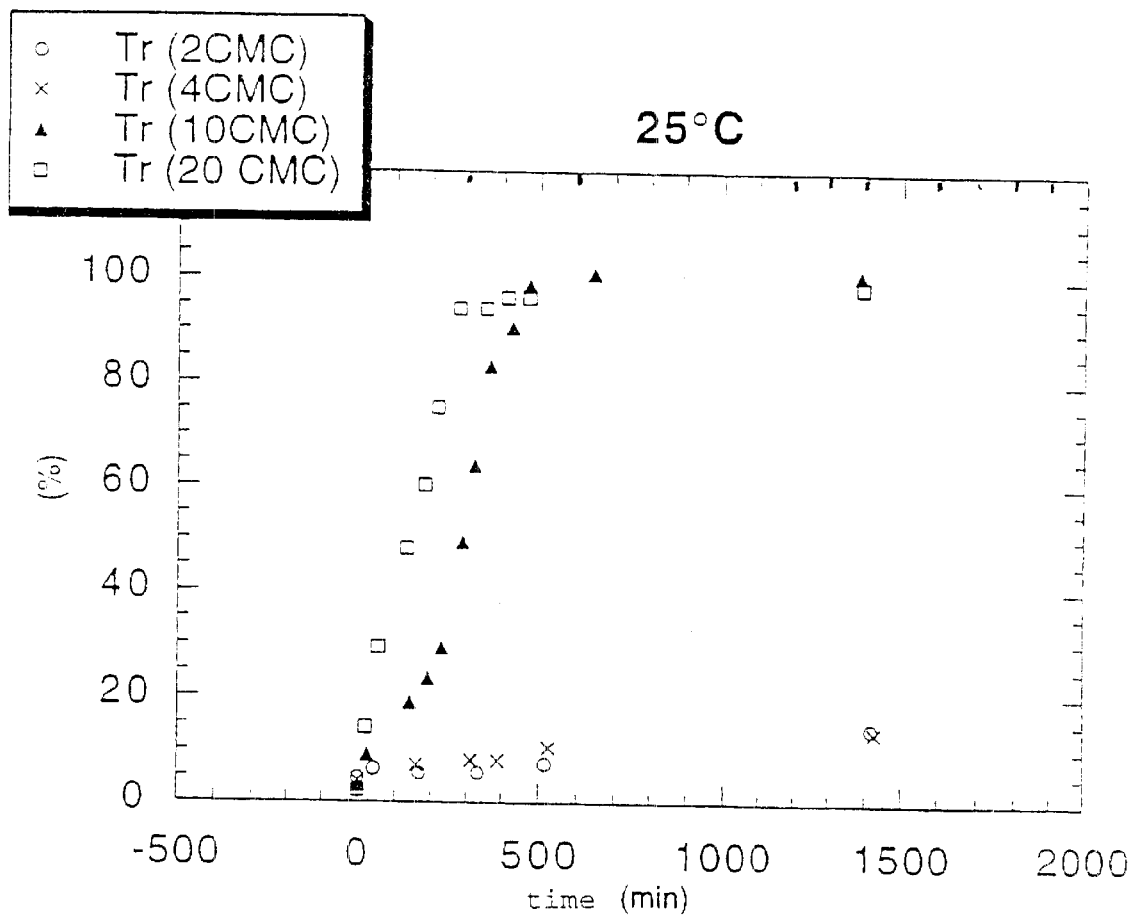
FIG. 1: Determination of the critical concentration threshold of a surfactant in a multiple emulsion.

According to a favoured embodiment of the invention, this agent is preferably a surfactant which is identical to the surfactant which is present in the aqueous phase A2 of the emulsion Ed and which is as defined below. Because of its presence, it shifts the initial concentration of this surfactant beyond its critical concentration threshold and thus triggers the coalescence phenomenon favourable to the release of the active principle.

However, it is also possible to envisage this release being induced by an agent with a nature different from that of the surfactant employed in the aqueous phase A2. It can thus be another surfactant or alternatively a compound already present in the external environment into which the release of the active principle is envisaged.

This agent can in particular be a polymer of polyvinylpyrrolidone or polyethylene glycol type or alternatively a hydrocolloid, such as xanthan gum, guar or carrageenan, and their derivatives.

The surfactant present in the aqueous phase A2 is preferably a water-soluble surfactant having an HLB of greater than 14.

Mention may in particular be made, as illustrations of water-soluble agents of this type, of lecithins which are soluble in water, sucrose esters, fatty acid esters (including the "Tweens"), polyoxyethylenated alkylamides, triglyceride sulphates, alkyl sulphates (including sodium dodecyl sulphate, SDS), alkyl ether sulphates, alkyl sulphonates, alkylamine salts (including Tetradecyl Trimethylammonium Bromide, TTAB), fatty amines, lipoamino acids (including bovine or human serum albumin, beta-lactoglobulin or casein), alkyl betaines, alkyl polyglycol ethers, alkylene oxide copolymers, modified polyesters and polymeric silicone surface-active agents.

As regards the surfactant present in the continuous oily phase of the emulsion Ei, it is preferably a fat-soluble surfactant with an HLB of less than 7.

The fat-soluble surfactants which can be employed in the emulsion according to the invention can be selected from lecithins which are soluble in fat, esters of sorbitan and fatty acids (including the "Span" esters), polyalkylene dipolyhydroxystearates, fatty acids, monoglycerides, polyglycerol esters, polyglycerol polyricinoleate and esters of lactic and tartaric acid.

The continuous phase of the emulsion Ei is an oily phase preferably composed of at least one oil selected from vegetable, animal or mineral oils.

The inverse emulsion Ei preferably comprises approximately 50% to 99% by volume of this continuous phase per 1% to 50% of aqueous phase A1.

As for the direct emulsion Ed, it preferably comprises from 50% to 99% by volume of aqueous phase A2 per 1% to 50% of this inverse emulsion Ei.

As regards the hydrophilic active principle present in the claimed emulsion, it can be a compound which is active in one of the following fields, namely pharmaceutical, cosmetic, plant-protection or foodstuff fields, and/or surfacings of paint or road type, for example.

It can thus be selected from vitamins (E, C), enzymes, insulin, analgesics, antimitotics, anti-inflammatories or antiglaucomas, vaccines, anti-cancer agents, narcotic antagonists, detoxification agents (salicylates, barbiturates), depilatory agents, agents for correcting or masking taste, water-soluble salts, breaking agents (bitumen emulsions), acids, bases, vinegar, glucose, colorants, preservatives or their mixtures.

Of course, the concentration of this active principle in the aqueous phase A1 is to be defined in each specific case by a person skilled in the art according to the expected effectiveness.

The invention is of particular use in accelerating the breaking of bitumen emulsions when they are spread over carriageways. In this specific application, a breaking agent, generally a salt or solution at basic pH, is incorporated in a multiple emulsion and its release is brought about by bringing the said emulsion into contact with the bitumen emulsion. In this specific case, it is the presence of the surfactant present in the bitumen emulsion which initiates the release of this breaking agent. This therefore results in an acceleration in the breaking of the bitumen, induced specifically by this breaking agent.

The present invention is targeted in particular at the application of the claimed process in the release of a breaking agent in the field of road surfacing and more particularly in the context of the application of a bitumen-based surfacing.

In another field of activity, such as that of pharmaceuticals, the invention also makes possible the release time of the active principle.

This is advantageous in two respects; it results in better assimilation of the active principle by the treated organism and an optimisation in the effectiveness of the active principle.

The examples and figures presented below are given by way of illustration and without implied limitation of the present invention.

EXAMPLE 1

Preparation of a Multiple Emulsion Stabilized by a Surfactant with an HLB Equal to 40 in the Aqueous Phase A2

In a first step, a monodisperse water-in-dodecane inverse emulsion which is stabilized with Span 80® (sorbitan monooleate from the company Sigma) is prepared. This emulsion is prepared by slowing introducing the disperse aqueous phase (80% by volume) with gentle shearing (of the order of 1000 $s^{-1}$) into a continuous phase composed of a dodecane/Span 80 mixture in a 1/1 ratio by weight. Sodium chloride NaCl (0.1M), intended to simulate the presence of the active principle in the aqueous phase A1, is added. Advantageously, it has been shown that the presence of this salt reinforces the stability of the inverse emulsion Ei (Aronson M. P., Petko M. F., J. Colloid Interface Sci., 1993, 159, 134). The initial polydisperse emulsion is converted by a fractional crystallisation technique (Bibette J., J. Colloid Interface Sci., 1991, 147, 474) into a monodisperse emulsion.

The diameter of the drops is approximately 0.3 µm.

The stability of this emulsion was tested over time. Likewise, the addition of a surfactant up to a concentration of 2% by mass, at a temperature of 20° C., to the emulsion, which is diluted in dodecane in a proportion of 10% by volume, does not induce any phase separation or phenomenon of aggregation.

Several multiple emulsions were subsequently prepared from this inverse emulsion by mixing it with an aqueous solution comprising sodium dodecyl sulphate (SDS, HLB= 40) at various concentrations below or greater than its critical micelle concentration, which is $8 \times 10^{-3}$ mol/l.

The test consists in carefully bringing together (over an area of 1 $cm^2$) equivalent volumes (1 $cm^3$) of the inverse emulsion and of water comprising variable amounts of SDS surfactant and a concentration of $AgNO_3$ at a concentration of $10^{-3}$ mol/l. The transfer of the water present in the inverse droplets to the macroscopic aqueous phase is detected by observation of an AgCl precipitate which is formed at the macroscopic interface when the internal contents transfer to the external phase. This is because, when the water droplets move via a coalescence phenomenon from the upper inverse emulsion to the lower aqueous phase, the upper phase gradually becomes transparent whereas the lower phase gradually becomes milky. It is observed that, for a concentration of SDS of less than approximately 10 CMC, the water droplets do not transfer to the second phase, even for a time lasting several days.

Above this limit concentration, the water droplets quickly transfer (in less than 48 hours) within the second phase.

In order to reduce the time period for diffusion through the upper phase, the same test was repeated with gentle centrifuging. By applying an acceleration of the order of $10^{-4}$ g (g being the acceleration of gravity) for 15 minutes, the drops of the inverse emulsion are either concentrated at the water/oil interface or transfer to the lower aqueous phase. Transfer via the coalescence phenomenon takes place for the same concentration within the lower aqueous phase, that is to say 10 CMC of SDS.

EXAMPLE 2

Determination of the Critical Concentration Threshold of a Surface-active Agent in a Multiple Emulsion The purpose of this study is to quantitatively monitor the release of a salt present in a double emulsion.

I. Production of a monodisperse double emulsion

The double emulsion is prepared in two stages.
1st Stage
A monodisperse water-in-dodecane inverse emulsion which is stabilized with Span 80 is prepared.

The aqueous phase (80% by volume) is introduced with gentle shearing (of the order of $1000 \, s^{-1}$) into a continuous phase composed of a dodecane/Span mixture (1:1 by mass). The aqueous phase comprises 1 mol per liter of potassium chloride. This salt acts as active substance which has to be released. The initial polydisperse emulsion is converted by a fractional crystallisation technique, so as to obtain a monodisperse emulsion (Bibette J., J. Colloid Interface Sci., 1991, 147, 474).

The characteristics of the inverse emulsion obtained after dilution are:

Fraction by volume of saline water: $\phi_{iv}$=10%.
Concentration by mass of Span 80 in dodecane=2 m %.
Diameter of the droplets: $\sigma_i$=0.3 µm.

2nd Stage

The preceding inverse emulsion is emulsified in its turn in an aqueous phase comprising a hydrophilic surface active agent (SDS). A double emulsion is thus obtained composed of oily globules comprising water droplets, which droplets result from the first stage.

The double emulsion is manufactured using a microfluidizer (Jet homogenizer from Labplant). This method consists in bringing the disperse phase and the continuous phase into contact under very high pressure and in then injecting the mixture via a hole with a small diameter (0.1 mm).

The characteristics of the double emulsion obtained are:

Fraction by volume of inverse emulsion: $\phi_{iv}$=20%.
Concentration of SDS in the external aqueous phase: $C_{SDS}$=CMC/10.
Mean size of the globules=4 µm.

II. Study of the Release of the Salt

II.1. Principle of the Potentiometric Quantitative Determination

The concentration of the KCl initially incorporated in the internal aqueous phase of the double emulsion is measured in the external aqueous phase by potentiometry.

The potentiometric quantitative determination is based on the measurement of a difference in potential between an indicator electrode (Ag/AgCl) and a reference electrode (mercurous sulphate electrode) which are immersed in the colloidal solution comprising the electrolyte to be quantitatively determined (Cl⁻ ion). The concentration of the Cl⁻ ion is in this case directly related to the potential ΔE of the Ag/AgCl electrode by a relationship of the type:

$$\Delta E = \beta + \alpha \log C_q \text{ (Nernst relationship)}.$$

It is then possible, via a calibration line, to know at any moment the concentration of Cl⁻ ion released into the external aqueous phase.

The results obtained are presented in graphical form in FIG. 1.

The abscissa of the curve represents the time, expressed in minutes, and the ordinate represents the percentage of salt released into the external aqueous phase.

The kinetics obtained demonstrate, with the microscopic observations, two scenarios for release of the salt.

In one of the cases, for an SDS concentration of greater or equal to 10 CMC, it is found that the release takes place rapidly (time corresponding to complete release of the salt of less than 500 minutes) and that the release becomes faster the greater the SDS concentration. In this case, conversion of the double emulsion into a simple emulsion (absence of droplets in the globules) is observed by optical microscopy. It is deduced from this that release by coalescence is taking place.

Conversely, when the SDS concentration is less than the concentration threshold of 10 CMC, it is noted that the release of the salt into the external aqueous phase is very slow. This release takes place by passive diffusion and not by coalescence, as the emulsion retains its double nature.

EXAMPLE 3

Influence of the Concentration of Surfactant in the Direct Emulsion on the Stability of the Multiple Emulsion In this test, a multiple emulsion is prepared by dispersing the inverse emulsion in a continuous aqueous phase comprising the SDS surfactant at a concentration equal to one tenth of its critical micelle concentration. The inverse phase is the same as that described above in Example 1: the fraction by volume of water drops is present therein at a concentration of 10% by volume with 0.1 mol/l of NaCl for a concentration of surfactant of 2%. The multiple emulsion is therefore composed of 90% by volume of an external aqueous phase and of 10% of the inverse phase. A high degree of shearing, of the order of 10,000 revolutions per minute, is applied using an Ultra-turrax device for 10 seconds to a total volume of 50 m³ of the overall composition, which results in the appearance of double drops in which the water content and the size of the droplets are retained.

Double drops are observed, with each of them comprising small inverse water drops. No phenomenon of coalescence between the big double globules is observed at this SDS concentration after storage for two months.

This test is repeated, the concentration of the surfactant within the external aqueous phase $C_e$ being varied and the double emulsion being freshly prepared, and the duration of existence of the internal water droplets is recorded. It is thus observed that the double emulsion is retained (more than one month) or is converted into a direct emulsion (in a period of time of a few hours), according to the SDS concentration. This transition takes place for exactly the same concentration as that mentioned in Example 1, that is to say approximately 10 CMC. FIG. 3(a) represents the double emulsion immediately after its preparation for an SDS concentration of 10 CMC and FIG. 3(b) shows the same emulsion after 2 days. It is thus observed, under a microscope, that only phenomena of coalescence between the tiny inverse water drops and the interface of the direct drops are responsible for the change which is observed.

Furthermore, no phenomenon of coalescence of the inverse droplets within the double globule is recorded in the period of time of this test. Only a gradual decrease in the concentration of internal droplets is observed. From these observations, it therefore emerges that there exists no phenomenon of coalescence between these internal drops and that the only coalescence phenomena existing are those that exist between the tiny drops and the interface of the globules.

EXAMPLE 4

Preparation of a Multiple Emulsion Stabilized by a Surfactant with an HLB Equal to 15 Present in the Aqueous Phase A2

Multiple emulsions are prepared according to the procedure described in the preceding examples by using Tween 80 in the aqueous phase A2 as surfactant. Its HLB is 15 and its critical micelle concentration is $10^{-3}$ mol/l. The same type of result is observed. Transfer of the internal water droplets is also dependent on the concentration $C_e$ of the surfactant in the external phase. In this case, the limit concentration is approximately 200 CMC.

It is observed for this surfactant that the internal water droplets coalesce with one another. This instability appears rapidly and results in a few internal water drops with a greater surface area, still imprisoned in the oily globules.

EXAMPLE 5

Figure 2:
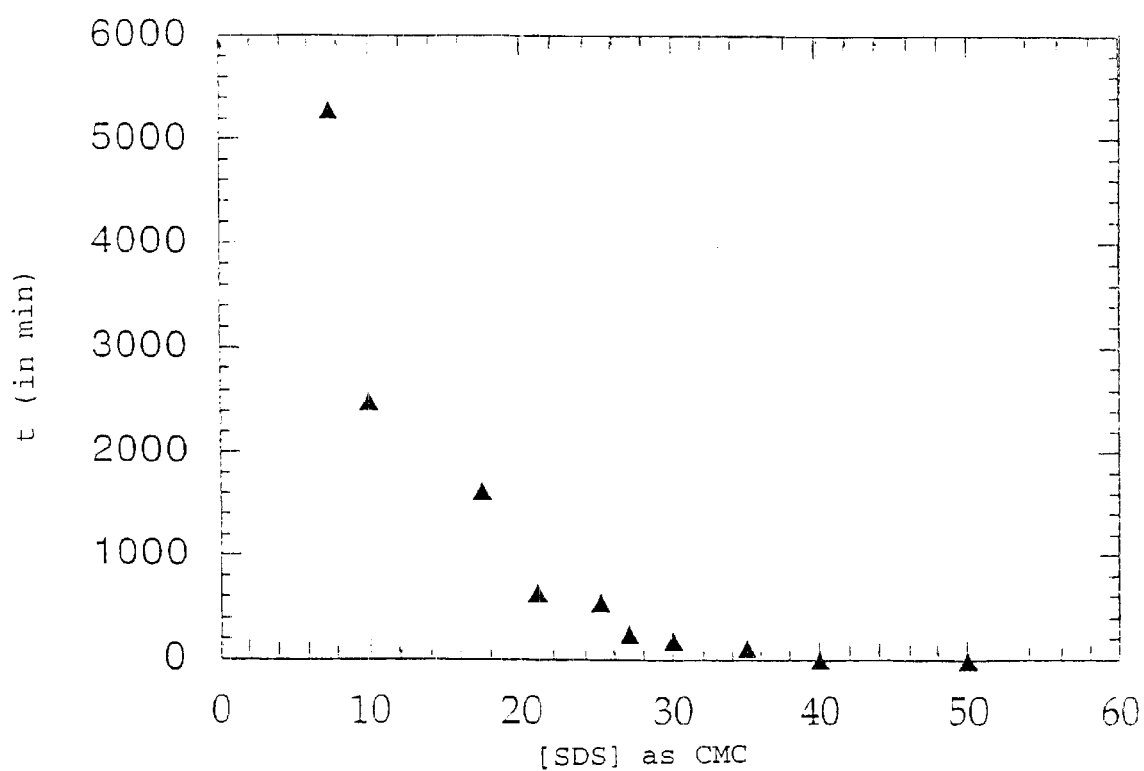
FIG. 2: Curve of release kinetics.

Determination of the Effect of the Concentration of Surfactant in the Aqueous Phase A2 on the Value of the Concentration Threshold Various emulsions are prepared according to the procedure defined in Example No. 1. The concentration of the surface-active agent (SDS) present in the external aqueous phase is varied and the change over time of the double emulsion is observed with a phase-contrast optical microscope (Zeiss Axiovert 100). The curve in FIG. 2 describes the change in the characteristic release time as a function of the concentration of surface-active agent present in the external aqueous phase. The characteristic release time is defined as the time at the end of which virtually all the droplets of phase A1 have been released into the external aqueous phase A2 (by coalescence). As indicated, this time is assessed visually using a microscope. It will be noted that the release time changes from several days, when the concentration is less than 10 CMC, to only a few hours, when the concentration is equal to 40 CMC.

What is claimed is:

1. A process for releasing an active principle comprising a multiple emulsion wherein the multiple emulsion comprises a water-in-oil-in water emulsion comprising an inverse emulsion Ei with an aqueous phase A1, in dispersion in the form of droplets of direct emulsion Ed, in a continuous aqueous phase A2, wherein the emulsion Ed is stabilized by a surfactant having an HLB of greater than 14 present in its continuous phase; the emulsion Ei is stabilized by a surfactant having an HLB of less than 7 present in its continuous phase; and the amount of the surfactant present in the aqueous phase A2 of the emulsion Ed is adjusted to an amount greater than the critical concentration threshold of this surfactant, for converting said multiple emulsion into a direct-emulsion, with a concentration threshold being between 7 and 20 CMC (Critical Micelle Concentration) for a surfactant having an HLB of the order of 40 and greater than 100 CMC for a surfactant having an HLB between 14 and 20 CMC; wherein the active principle is in solution in the aqueous phase A1 and said active principle is released into the aqueous phase A2 by adjusting the concentration of the surfactant present in said aqueous phase A2 with the release time being shorter at concentrations equal to or greater than this surfactant's critical concentration threshold.

2. The process according to claim 1, wherein an agent is added to the multiple emulsion, said agent is a surfactant identical to that present in the aqueous phase A2 of the emulsion Ed.

3. The process according to claim 1, wherein an agent is added to the multiple emulsion, said agent is a surfactant identical to that present in the aqueous phase A2 of the emulsion Ed and is introduced in an amount sufficient for its concentration in the aqueous phase A2 to be greater than its critical concentration threshold.

4. The process according to claim 1, wherein the surfactant present in the continuous aqueous phase A2 of the emulsion Ed is selected from the group consisting of lecithins which are soluble in water, sucrose esters, fatty acid esters, polyoxyethylenated alkylamides, triglyceride sulphates, alkyl sulphates, alkyl ether sulphates, alkyl sulphonates, alkylamine salts, fatty amines, lipoamino acids, alkyl betaines, alkyl polyglycol ethers, alkylene oxide copolymers, modified polyesters and polymeric silicone surface-active agents.

5. The process according to claim 1, wherein the surfactant present in the continuous phase of the emulsion Ei is selected from the group consisting of lecithins which are soluble in fats, esters of sorbitan and fatty acids, polyalkylene dipolyhydroxystearates, fatty acids, monoglycerides, polyglycerol esters, polyglycerol polyricinoleate and esters of lactic and tartaric acid.

6. The process according to claim 1, wherein the continuous phase of the emulsion Ei is an oily phase composed of at least one oil selected from the group consisting of mineral, vegetable and animal oils.

7. The process according to claim 1, wherein the active principle in solution in the aqueous phase A1 is a compound selected from the group consisting of vitamins, enzymes, insulin, analgesic, antimitotics, anti-inflammatories or antiglaucomas, vaccines, anti-cancer agents, narcotic antagonist, detoxification agents, depilatory agents, agents for correcting or masking taste, water-soluble salts, breaking agents, acids, bases, vinegar, glucose, colorants, preservatives or their mixtures.

8. The process according to claim 1, wherein the direct emulsion Ed comprises, by volume, from 50 to 99% of a continuous aqueous phase A2 per 1 to 50% of inverse emulsion Ei.

9. The process according to claim 1, wherein the inverse emulsion Ei is preferably composed, by volume, of 50 to 99% of a continuous phase per 1 to 50% of aqueous phase $A_1$.

* * * * *